(12) United States Patent
Belef et al.

(10) Patent No.: US 6,796,945 B2
(45) Date of Patent: Sep. 28, 2004

(54) INTRAVASCULAR IMAGING GUIDEWIRE

(75) Inventors: William Martin Belef, San Jose, CA (US); Anthony J. Pantages, Los Altos, CA (US); Lawrence D. Wasicek, San Jose, CA (US)

(73) Assignee: SciMed Life Systems, Inc., Maple Grove, MN (US)

( * ) Notice: Subject to any disclaimer, the term of this patent is extended or adjusted under 35 U.S.C. 154(b) by 0 days.

(21) Appl. No.: 10/216,119

(22) Filed: Aug. 8, 2002

(65) Prior Publication Data

US 2002/0188189 A1 Dec. 12, 2002

Related U.S. Application Data

(63) Continuation of application No. 09/579,714, filed on May 26, 2000, now Pat. No. 6,459,921, which is a continuation of application No. 08/939,315, filed on Sep. 29, 1997, now Pat. No. 6,078,831.

(51) Int. Cl.[7] .............................. A61B 5/00; A61B 8/12
(52) U.S. Cl. ....................................... 600/467; 600/585
(58) Field of Search ................................ 600/407, 467, 600/585, 462, 463

(56) References Cited

U.S. PATENT DOCUMENTS

| | | | |
|---|---|---|---|
| 4,794,931 A | 1/1989 | Yock | 128/660.03 |
| 4,934,380 A | 6/1990 | de Toledo | 600/585 |
| 4,961,433 A | 10/1990 | Christian | 128/772 |
| 5,065,769 A | 11/1991 | de Toledo | 600/585 |
| 5,095,911 A | 3/1992 | Pomeranz | 128/662.06 |
| 5,178,159 A | 1/1993 | Christian | 128/772 |
| 5,240,437 A | 8/1993 | Christian | 439/668 |
| 5,243,988 A | 9/1993 | Sieben et al. | 128/662.06 |
| 5,353,798 A | 10/1994 | Sieben | 128/662.06 |
| 5,368,035 A | 11/1994 | Hamm et al. | 128/662.06 |
| 5,372,138 A | 12/1994 | Crowley et al. | 600/463 |
| 5,373,849 A | 12/1994 | Maroney et al. | 128/662.06 |
| 5,421,338 A | 6/1995 | Crowley et al. | 128/662.06 |
| 5,438,997 A | 8/1995 | Sieben et al. | 128/662.06 |
| 5,454,373 A | 10/1995 | Koger et al. | 128/662.06 |
| 5,464,016 A | 11/1995 | Nicholas et al. | 128/662.06 |
| 5,507,301 A | 4/1996 | Wasicek et al. | 128/772 |
| 5,520,189 A | 5/1996 | Malinowski et al. | 128/662.03 |
| 5,546,948 A | 8/1996 | Hamm et al. | 128/662.06 |
| 5,827,313 A | 10/1998 | Ream | 606/171 |
| 5,855,563 A | 1/1999 | Kaplan et al. | 604/49 |
| 5,865,178 A | 2/1999 | Yock | 128/660.03 |
| 5,868,767 A | 2/1999 | Farley et al. | 606/159 |
| 5,873,835 A | 2/1999 | Hastings et al. | 600/488 |
| 5,879,305 A | 3/1999 | Yock et al. | 600/462 |
| 5,951,480 A | 9/1999 | White et al. | 600/463 |
| 5,957,899 A | 9/1999 | Spears et al. | 604/264 |
| 6,078,831 A * | 6/2000 | Belef et al. | 600/424 |
| 6,261,246 B1 * | 7/2001 | Pantages et al. | 600/585 |
| 6,459,921 B1 * | 10/2002 | Belef et al. | 600/407 |
| 6,529,760 B2 * | 3/2003 | Pantages et al. | 600/407 |

* cited by examiner

Primary Examiner—Shawna J. Shaw
(74) Attorney, Agent, or Firm—Orrick, Herrington & Sutcliffe, LLP

(57) ABSTRACT

An intravascular imaging guidewire is provided that can accomplish longitudinal translation of an imaging plane allowing imaging of an axial length of a region of interest without moving the guidewire. The imaging guidewire comprises a body in the form of a flexible elongate tubular member. An elongate flexible imaging core is slidably received within the body. The imaging core includes a shaft having an imaging device mounted on its distal end. The body and the imaging core are cooperatively constructed to enable axial translation of the imaging core and imaging device relative to the body. The body has a substantially transparent portion extending an axial length over which axially translatable imaging may be performed. The imaging guidewire has a maximum diameter over its entire length sized to be received within a guidewire lumen of an intravascular catheter.

7 Claims, 8 Drawing Sheets

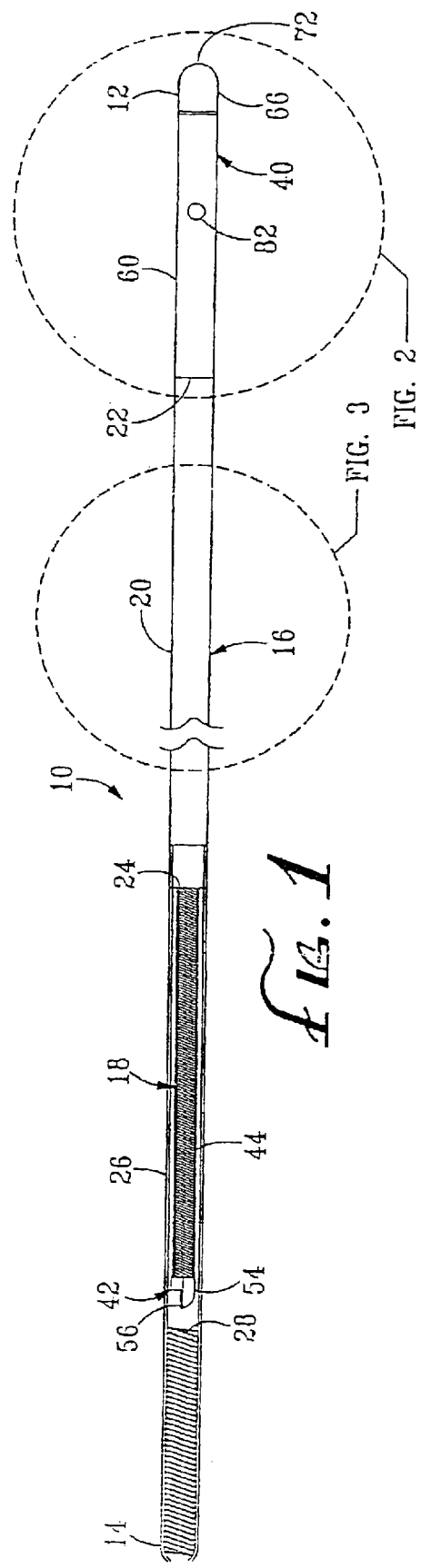
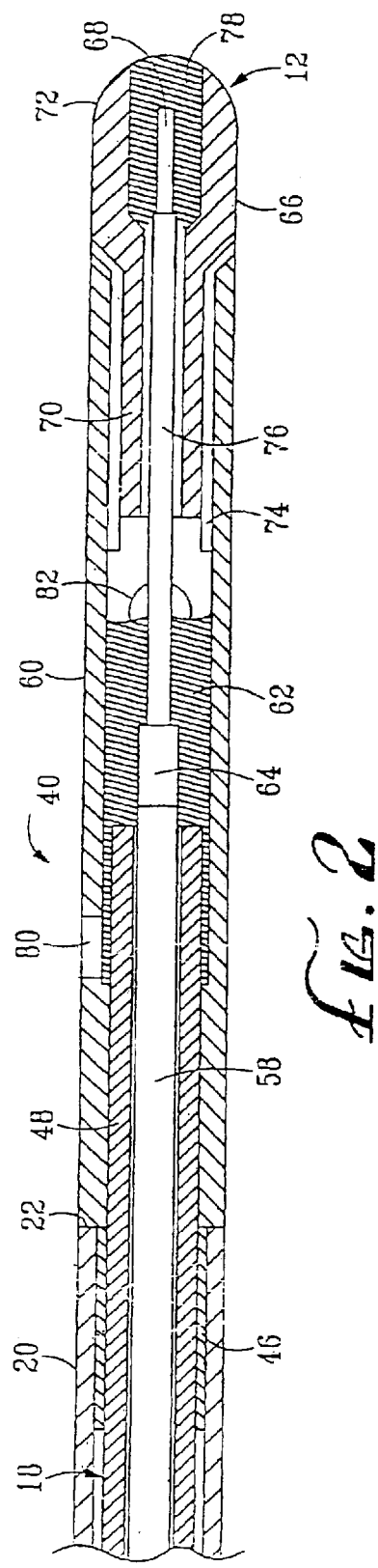

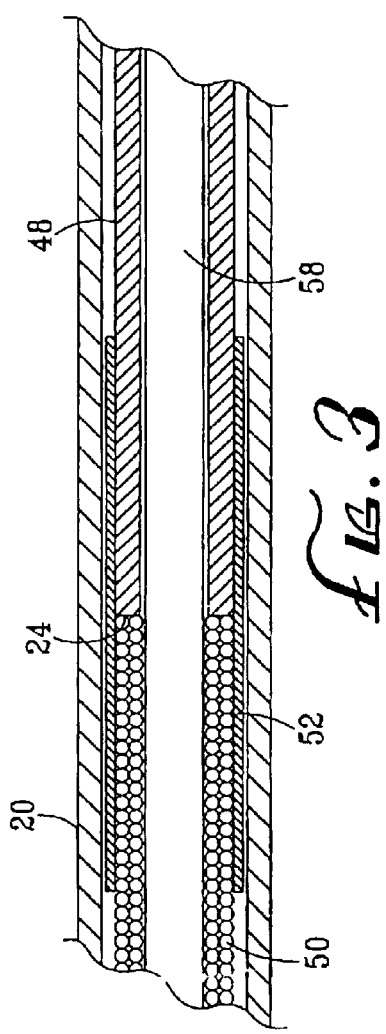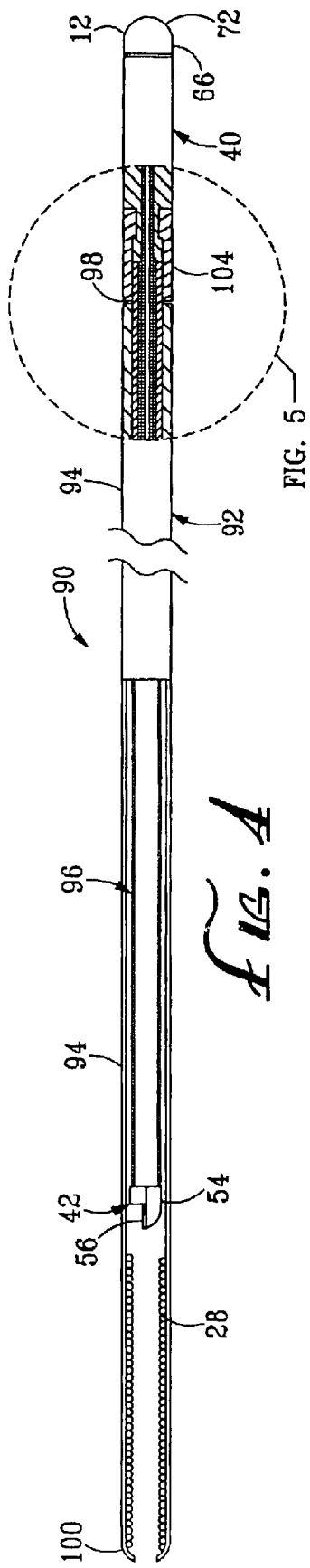

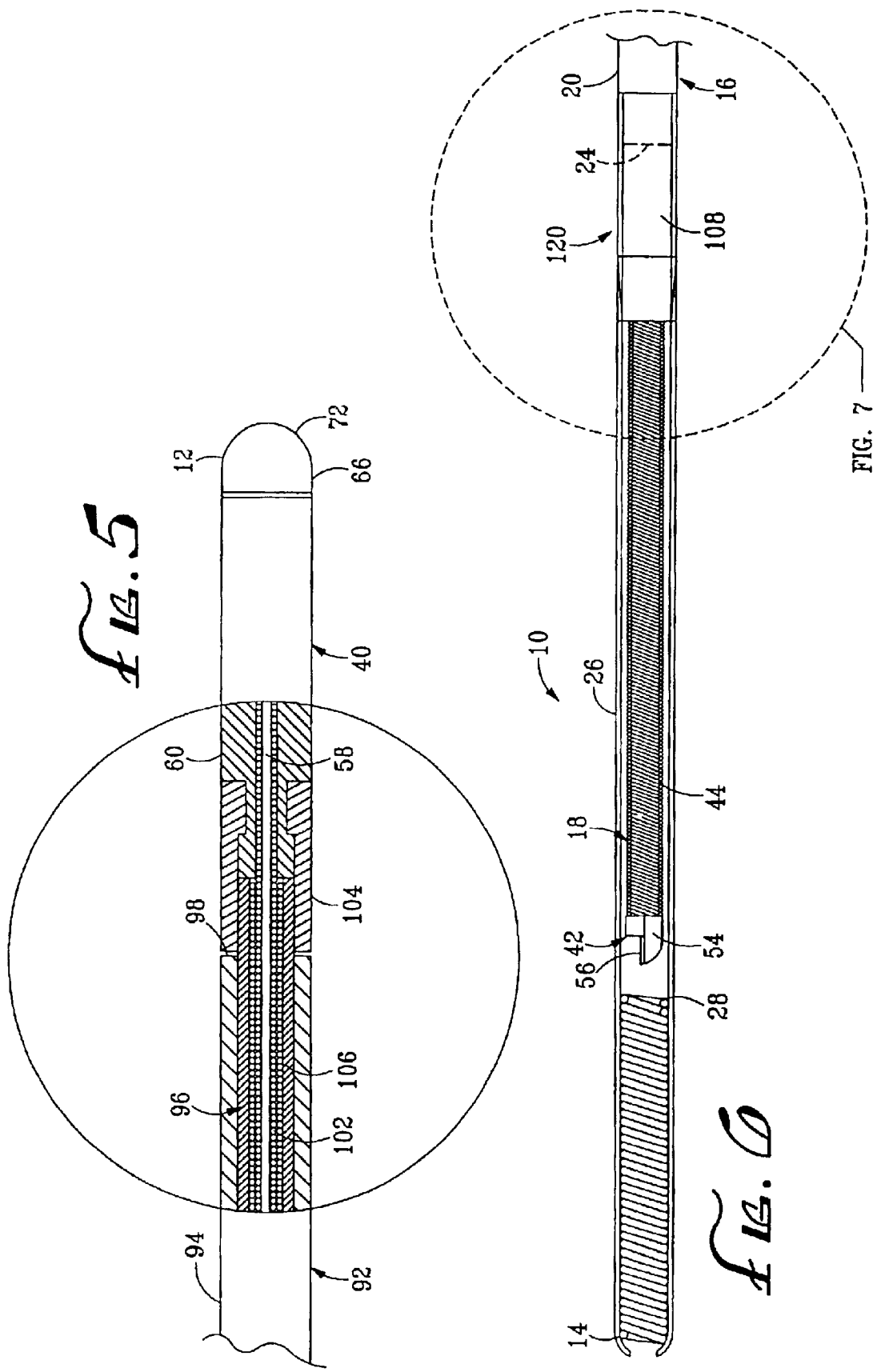

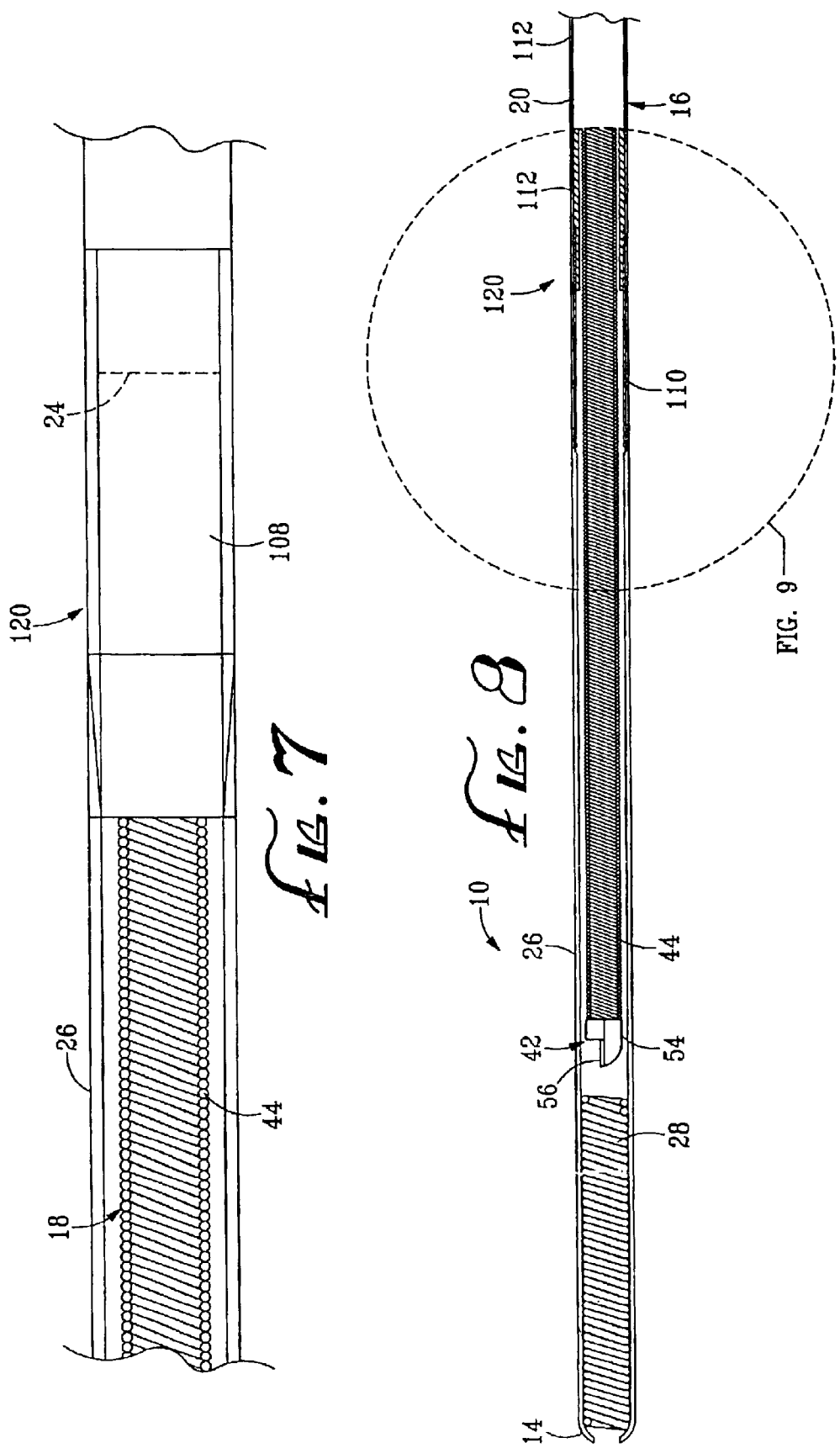

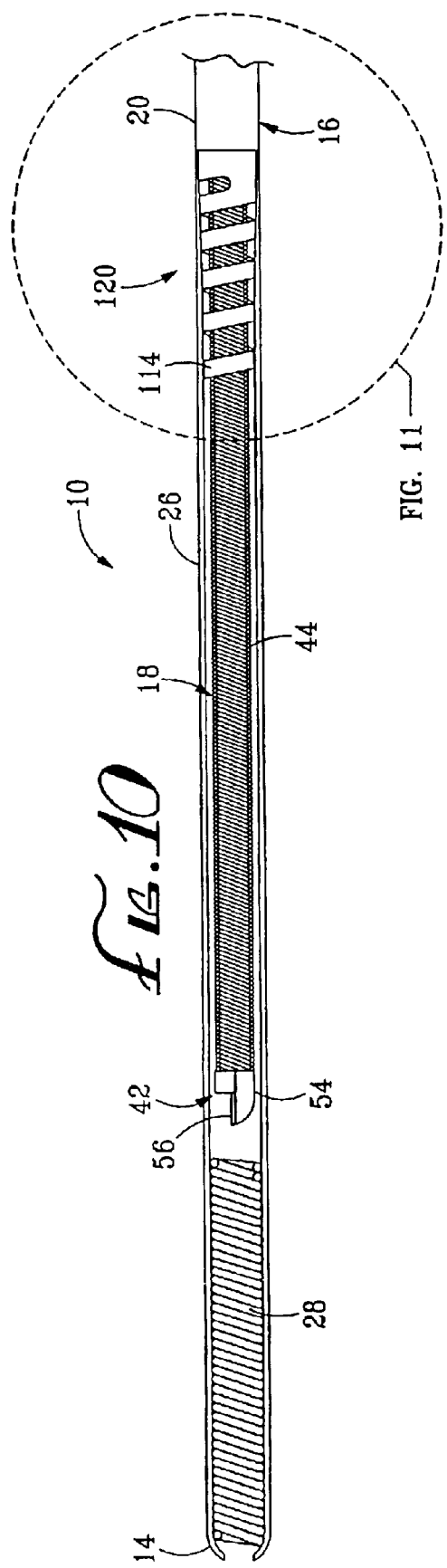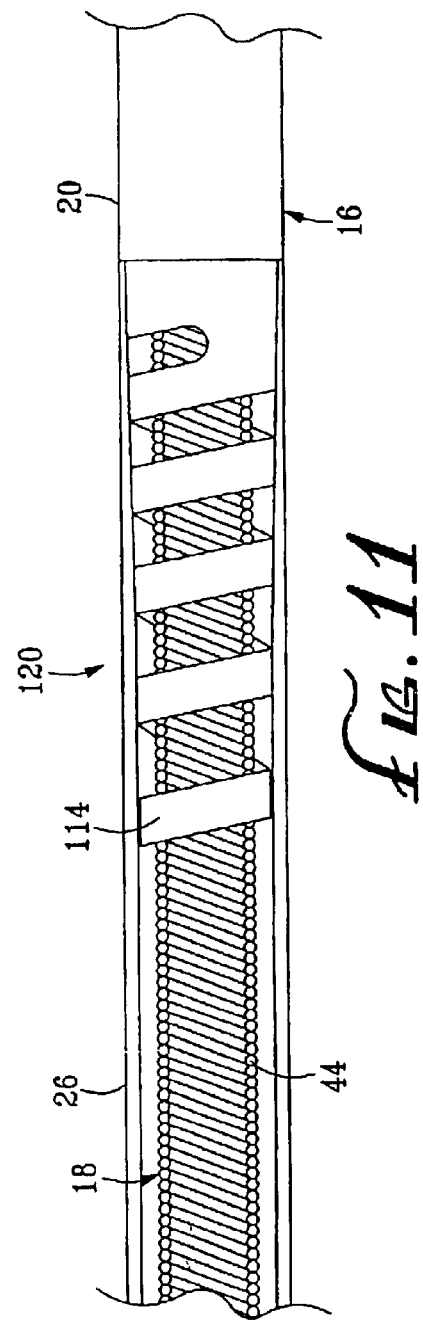

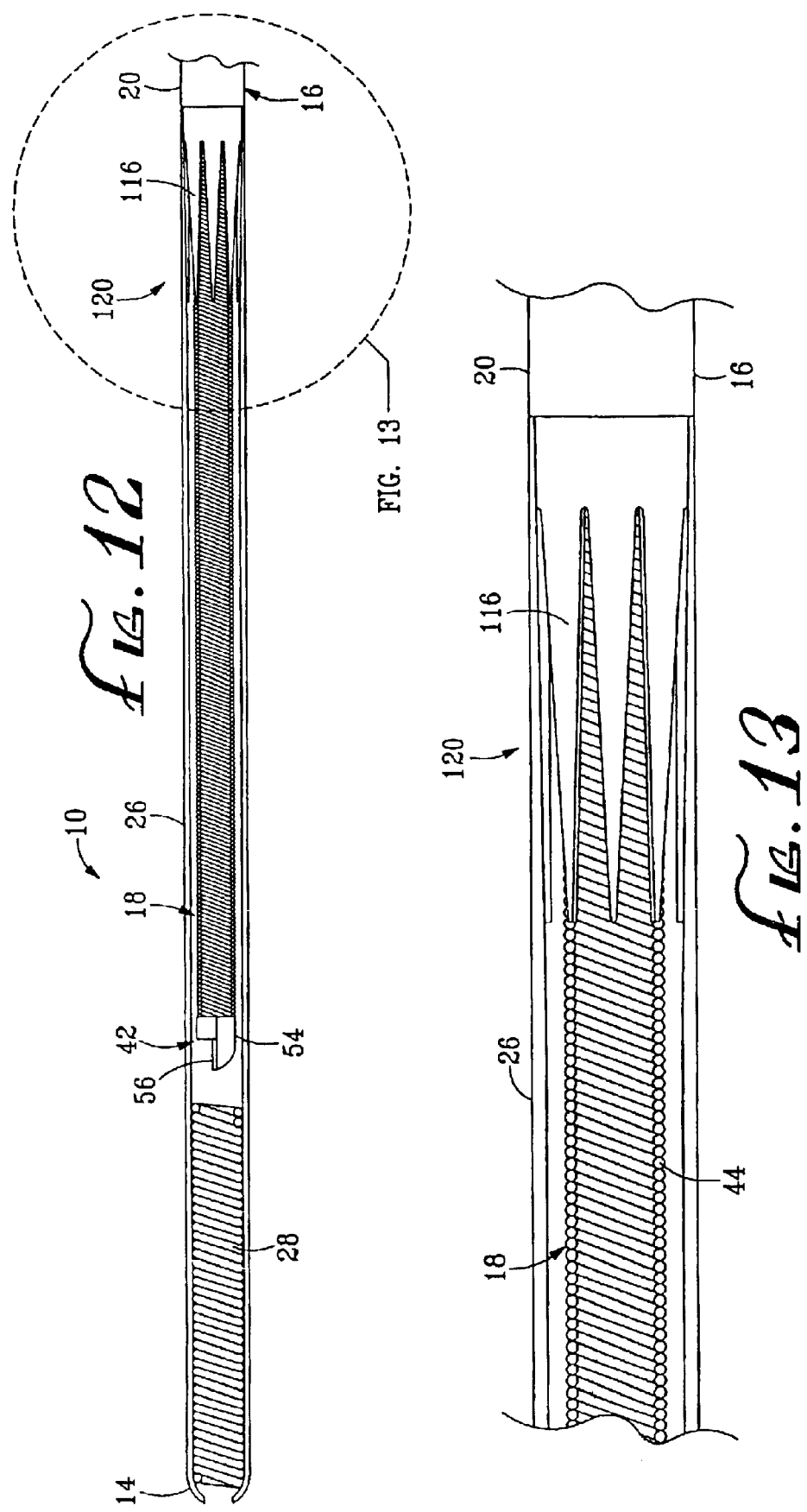

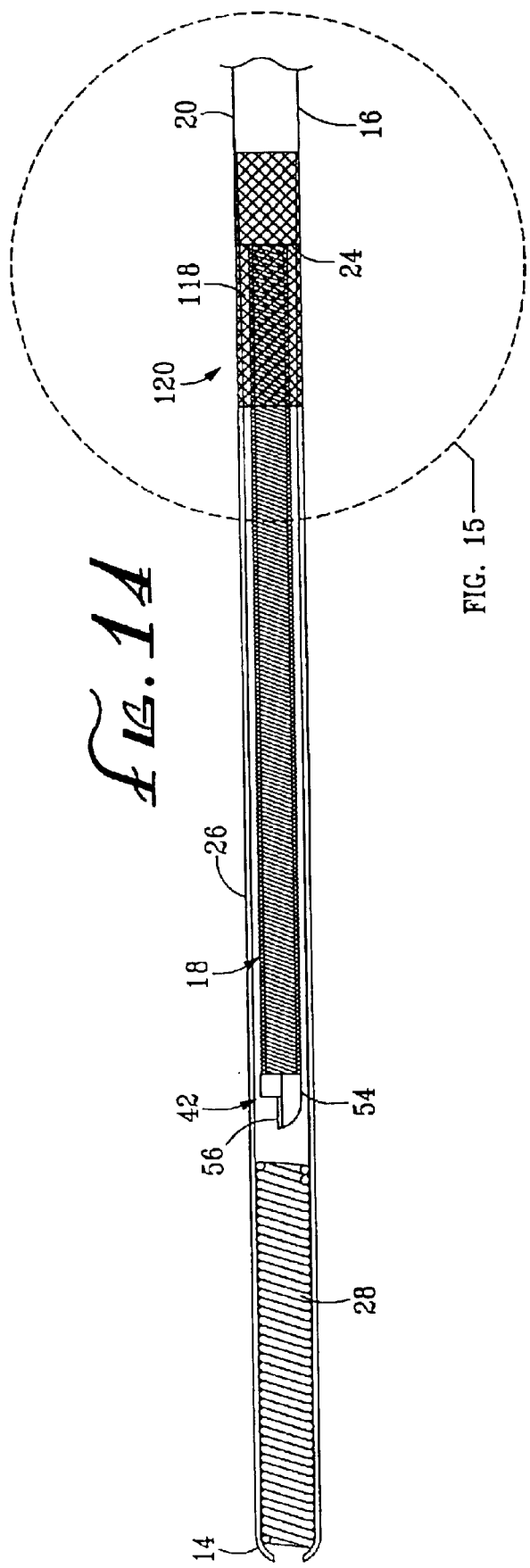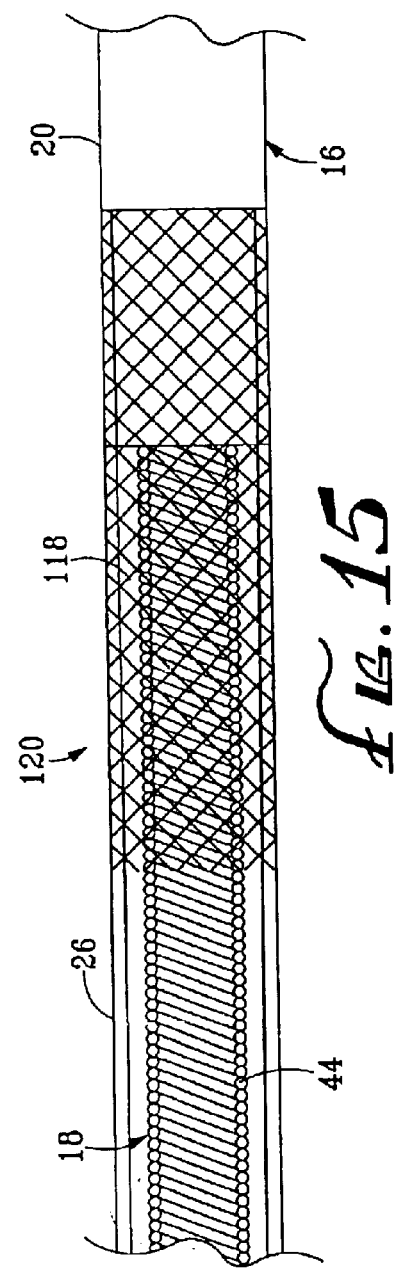

INTRAVASCULAR IMAGING GUIDEWIRE

This Application is a continuation of U.S. application Ser. No. 09/579,714, filed on May 26, 2000 now U.S. Pat. No. 6,459,921, now allowed, which itself is a continuation of U.S. application Ser. No. 08/939,315, filed on Sep. 29, 1997, now issued as U.S. Pat. No. 6,078,831, all of which are incorporated by reference as if set forth fully herein.

FIELD OF THE INVENTION

The present invention relates to an intravascular imaging device and methods for use and manufacture thereof, and more specifically to an imaging guidewire which can be used to receive a therapeutic catheter having a guide lumen to direct the catheter to a desired position within a vessel of a body.

BACKGROUND OF THE INVENTION

Intraluminal, intracavity, intravascular, and intracardiac treatment and diagnosis of medical conditions utilizing minimally invasive procedures is an effective tool in many areas of medical practice. These procedures are typically performed using imaging and treatment catheters which are inserted percutaneously into the body and into an accessible vessel of the vascular system at a site remote from the vessel or organ to be diagnosed and/or treated, such as the femoral artery. The catheter is then advanced through the vessels of the vascular system to the region of the body to be treated. The catheter may be equipped with an imaging device, typically an ultrasound imaging device, which is used to locate and diagnose a diseased portion of the body, such as a stenosed region of an artery. The catheter may also be provided with a therapeutic device, such as those used for performing interventional techniques including balloon angioplasty, laser ablation, atherectomy and the like. Catheters are also commonly used for the placement of grafts, stents, stent-grafts, etc. for opening up and/or preventing closure of diseased or damaged vessels.

Catheters having ultrasound imaging and/or therapeutic capabilities are generally known. For example, U.S. Pat. No. 5,313,949, issued to Yock, the disclosure of which is incorporated herein by reference, describes an intravascular ultrasound imaging catheter having an atherectomy cutting device. Generally speaking, there are two predominant techniques used to position the therapeutic catheter at the region of interest within the body. The first technique simply involves directly inserting the catheter into a vessel and advancing the catheter through the branches of the vascular system by pushing and steering the catheter to enter a desired branch as the catheter is moved forward. The use of this technique typically requires that the catheter be equipped with an extremely flexible guidewire at its distal tip which can be aimed in different directions by rotating the catheter or by actuating a steering mechanism.

The second technique utilizes a separate guidewire which is first positioned within the vascular system such that a distal end of the guidewire extends beyond the region of interest. The guidewire is routed into position by inserting it into a vessel and advancing it through the vascular system by pushing and steering the guidewire similar to the method previously described for a catheter. The catheter being inserted includes a guidewire lumen which is sized to receive the guidewire. The guidewire lumen may extend the entire length of the catheter, or alternatively, the guidewire lumen may be a short length lumen disposed at the distal end of the catheter. Once the guidewire is in place, the therapeutic and/or imaging catheter is routed over the guidewire to the region of interest while holding the guidewire fixed in place.

The use of a guidewire provides several advantages. Routing a catheter or guidewire through a circuitous path of the complex network of blood vessels to a region of interest can be a tedious and time consuming task. Placement of the guidewire is made even more difficult with increasing vessel occlusion which may occur in the later stages of vascular disease. In addition, many catheter procedures require the use of several different catheters. For instance, an imaging catheter may be initially inserted to precisely locate and diagnose a diseased region. Then, the imaging catheter may be removed and a therapeutic catheter, such as an balloon angioplasty catheter, may be inserted. Additional therapeutic or imaging catheters may be employed as necessary. Accordingly the successive insertion and removal of each of these, catheters, called catheter "exchanges," is required because there is only enough space within the vessels to route a single catheter at a time. Hence, with the use of a guidewire, the tedious and time consuming task of routing a device to the region of interest need only be done once. Then, the much easier procedure of routing catheters over the guidewire to the region of interest may be performed as many times as the desired therapy dictates.

In order to locate the site of interest and facilitate proper placement of the guidewire, and further to observe the site during and after treatment, a guidewire may include an imaging device, commonly a rotating ultrasonic imaging transducer or a phased-array ultrasound transducer. Providing the guidewire with imaging capability may eliminate the need for insertion of an imaging catheter or imaging capabilities in the therapeutic catheters. Hence, an imaging guidewire can reduce the number of catheter exchanges that a physician must do during a surgical procedure.

Imaging guidewires have been disclosed generally, for example, in U.S. Pat. No. 5,095,911, issued to Pomeranz, the disclosure of which is incorporated herein by reference. The imaging guidewire disclosed in Pomeranz includes an elongate, flexible body. A housing enclosing a rotating transducer is secured to the distal end of the body. A drive shaft extends through a lumen of the body and is coupled to the transducer. In order to image a different region of interest, the entire guidewire is moved back and forth to position the housing and transducer adjacent the region.

However, once the physician has carefully placed the imaging guidewire, it is preferable to maintain the guidewire in a fixed position so as not to lose the correct placement of the guidewire. At the same time, it is often desirable to obtain images along an axial length of diseased area. This currently requires axial translation of the imaging device by axially translating the entire guidewire. The problem with advancing and pulling back the imaging guidewire is that the correct placement of the guidewire may be lost and the physician must then spend more time repositioning the guidewire.

Furthermore, there are significant technical obstacles in producing an imaging guidewire having a sufficiently small diameter to fit within a guidewire lumen of a catheter while at the same time exhibiting the necessary mechanical and electrical characteristics required for placement in the vascular system and generation of high quality images. For instance, on typical catheters sized to be inserted in the smaller coronary vessels, the guidewire lumen is sized to receive a guidewire having a maximum diameter of 0.035". In addition, the 0.035" guidewire must have sufficient flexibility to traverse a tortuous path through the vascular system, and also have sufficient column strength, or pushability, to transmit a pushing force from a remote proximal end of the guidewire, along a winding path, to the distal end thereof.

Moreover, if a rotating transducer is utilized, the drive shaft extending to the transducer must have stable torsional transmittance in order to achieve high quality images. Hence, the drive shaft must not only be flexible, but also must be torsionally stiff to limit angular deflection and nonuniform angular velocity which can cause image distortion. The drive shaft must also be mechanically and electrically connectable to a motor drive and transducer signal processing electronics. The connection must be easily disconnectable so that a guidewire lumen of a catheter may be threaded over the proximal end of the guidewire. This requirement also limits the size of the connector on the drive shaft because the connector must also fit through the guidewire lumen. The drive shaft and connector must also provide a high quality transmission of imaging signals between the imaging device and the signal processing equipment.

Therefore, a need exists for an improved imaging guidewire which overcomes the aforementioned obstacles and deficiencies of currently available guidewires.

SUMMARY OF THE INVENTION

The present invention provides an intravascular guidewire, and methods of use and manufacture, which can accomplish longitudinal translation of an imaging plane allowing imaging of an axial length of a region of interest without moving the guidewire thereby maintaining proper positioning of the guidewire to effectively facilitate the introduction of catheters over the guidewire to the proper position. Accordingly, the imaging guidewire of the present invention comprises a body in the form of a flexible, elongate tubular member. An elongate, flexible imaging core is slidably and rotatably received within the body.

The imaging core includes a rotatable drive shaft having an imaging device mounted on its distal end. The imaging device produces an imaging signal which can be processed by signal processing equipment to create an image of the feature at which the imaging device is directed. An electrical cable runs through the center of the drive shaft extending from the imaging device at the distal end to a connector attached to the proximal end of the drive shaft. The connector detachably connects the driveshaft to a drive unit and electrically connects the electrical cable to imaging signal processing equipment. At least a distal portion of the body through which the imaging device images is transparent to imaging signals received by the imaging device. The transparent portion of the body extends for at least an axial length over which imaging will typically be desirable.

The body and the imaging core are cooperatively constructed to enable axial translation of the imaging core and imaging device relative to the body. This allows imaging along an axial length of a diseased region in the body without moving the body.

In the preferred method of using the imaging guidewire of the present invention, the imaging guidewire is first inserted percutaneously into a vessel of the vascular system usually at a site remote from the site of interest within the body. The imaging guidewire is routed to the region of interest by advancing it through the branches of the vascular system by pushing and steering the guidewire as the guidewire is fed into the vessel. The imaging device may be activated during this process to aid in routing the guidewire and locating a diseased region of the body. The imaging guidewire is positioned such that the distal end extends beyond the diseased region with the transparent portion of the body approximately centered at the region of interest. Alternatively, a standard guidewire may first be inserted and routed to the region of interest. Then, a catheter having a full-length guidewire lumen is fully inserted over the standard guidewire. The standard guidewire is then removed and the imaging guidewire is inserted through the guidewire lumen to the desired position.

At this point, in order to image the length of the diseased region, the imaging device may be axially translated forward and back relative to the body which is preferably fixed in place.

Once the medical condition has been diagnosed and a treatment is chosen, a therapeutic catheter having a guidewire lumen, or a series of therapeutic catheters, may be routed over the guidewire to the diseased region to perform the desired treatment. The imaging device on the guidewire may further be used to monitor the treatment while it is being performed and/or to observe the treated area after the treatment is completed. Alternatively, if the imaging device cannot image through the therapeutic catheter, the catheter may be pulled back to expose the imaging device.

Accordingly, it is an object of the present invention to provide an improved imaging guidewire and method of using the same.

A further object of the present invention is to provide an improved imaging guidewire which can image along an axial length of a region of interest while maintaining a fixed guidewire position.

BRIEF DESCRIPTION OF THE DRAWINGS

FIG. 1 is a partial cross-sectional view of an imaging guidewire in accordance with the present invention.

FIG. 2 is an expanded cross-sectional view of the proximal region of the imaging guidewire as designated in FIG. 1.

FIG. 3 is an expanded cross-sectional view of the region as designated in FIG. 1.

FIG. 4 is a partial cross-sectional view of an alternative imaging guidewire in accordance with the present invention.

FIG. 5 is an expanded cross-sectional view of the region as designated in FIG. 4.

FIG. 6 is a partial cross-sectional view of another alternative imaging guidewire in accordance with the present invention.

FIG. 7 is an expandable cross-sectional view of the region as designated in FIG. 6.

FIG. 8 is a partial cross-sectional view of another alternative imaging guidewire in accordance with the present invention.

FIG. 10 is a partial cross-sectional view of yet another alternative imaging guidewire in accordance with the present invention.

FIG. 11 is an expandable cross-sectional view of the region as designated in FIG. 10.

FIG. 12 is a partial cross-sectional view of still another alternative imaging guidewire in accordance with the present invention.

FIG. 13 is an expandable cross-sectional view of the region as designated in FIG. 12.

FIG. 14 is a partial cross-sectional view of another alternative imaging guidewire in accordance with the present invention.

FIG. 15 is an expandable cross-sectional view of the region as designated in FIG. 14.

DETAILED DESCRIPTION OF THE INVENTION

Figure 9:
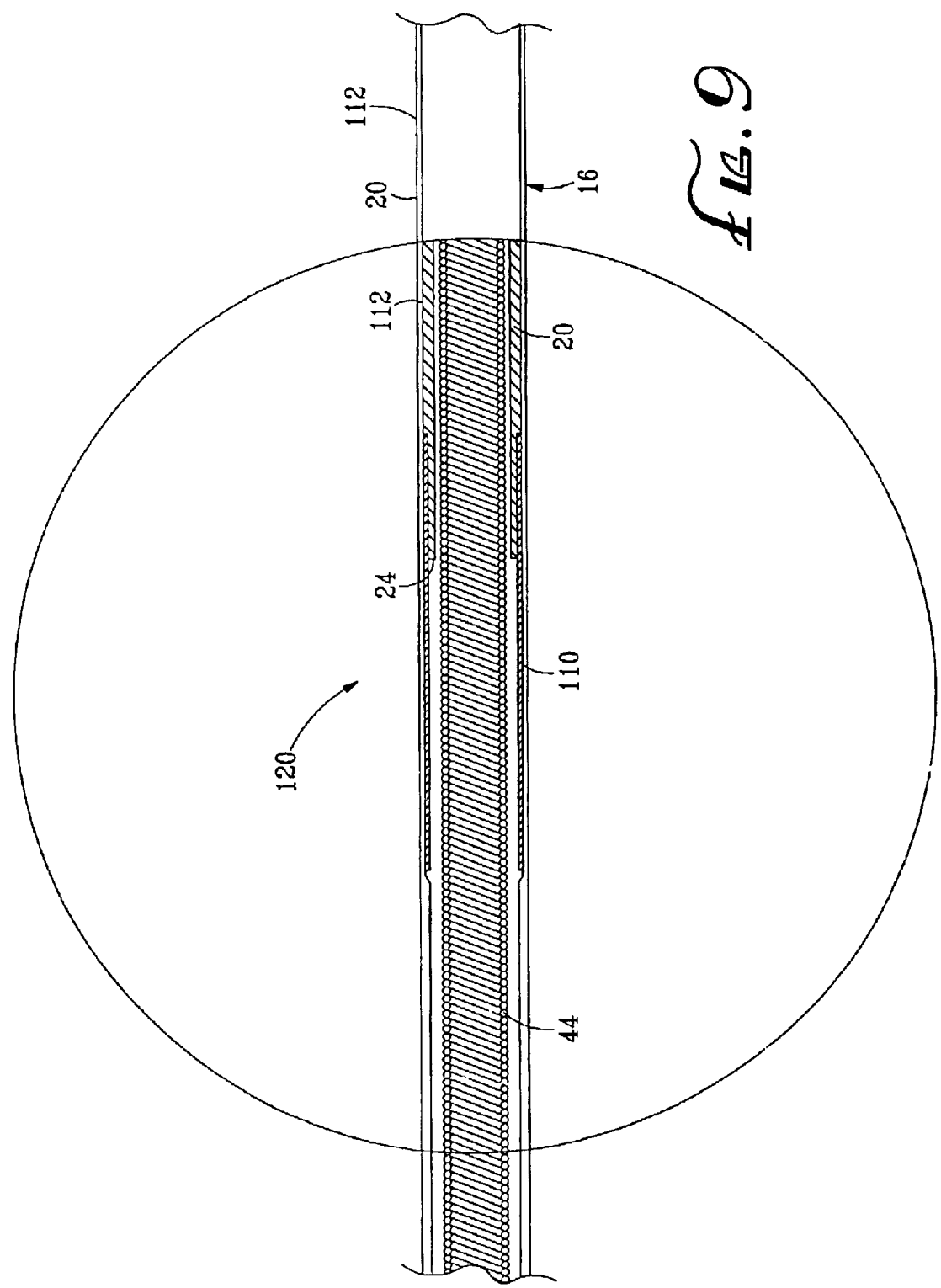
FIG. 9 is an expandable cross-sectional view of the region as designated in FIG. 8.

Referring to FIGS. 1–3, an imaging guidewire 10 is depicted according to the present invention. In general, the guidewire 10 must be flexible enough to traverse a circuitous path through the vascular system, and yet have sufficient pushability to transmit a pushing force from a remote proximal end 12 of the guidewire 10, along a winding path, to a distal end 14 of the guidewire 10. The imaging guidewire 10 must also have sufficient torsional stiffness to reliably transmit rotational force applied at the proximal end 12 to the distal end 14 so that the guidewire 10 can be steered through the branches of vessels of the vascular system.

The imaging guidewire 10 comprises a guidewire body 16 in the form of a flexible, elongate tubular member which slidably and rotatably houses an elongate, flexible, rotating imaging core 18. The imaging guidewire 10 has a substantially uniform diameter and no component along the entire length of the guidewire 10 exceeds a predetermined diameter. This maximum diameter is preferably 0.035" because guidewire lumens of typical catheters sized to be inserted into smaller vessels are sized to receive a guidewire having a maximum diameter of 0.035". The overall length of the guidewire 10 varies depending on the intended application but may preferably range between 40 cm and 300 cm.

The guidewire body 16 includes a main body 20 having a proximal end 22 and a distal end 24. The main body 20 extends from a connector 40 of the imaging core 18 at its proximal end 22 to a predetermined distance, preferably approximately 15 to 20 cm, from the distal end 14 of the guidewire 10 at its distal end 24. The main body 20 is preferably formed of NITINOL hypotube because it exhibits strength and flexibility properties desired in a guidewire body. NITINOL is also preferred because it minimizes kinking, has a convenient transition temperature below which is transitions to a "soft" state, and is a memory metal such that is returns to its original shape after being bent under specific temperature conditions. Those skilled in the art would appreciate that other materials including other superelastic materials, other metal alloys, and plastics may also be used. It is to be understood that where NITINOL is specified as the preferred material, other materials, including alternative superelastic materials, metal alloy, and plastics may also be utilized. The NITINOL main body 20 preferably has an outer diameter of approximately 0.035".

An imaging portion 26 of the guidewire body 16 is connected to the distal end 24 of the main body 20 and extends to the distal end 14 of the guidewire body 16. The imaging portion 26 is substantially transparent to imaging signals transmitted and/or received by an imaging device 42 of the imaging core 18. In a preferred form, the imaging portion 26 is formed of a polyethylene plastic tube which is interference fit onto the distal end 24 of the main body 20. Alternatively, any other suitable attachment method may be employed such as adhesives, mechanical connectors, etc.

A floppy tip 28 is placed inside, and at the distal end, of the imaging portion 26. The floppy tip 28 provides a flexible tip to assist in maneuvering the imaging guidewire 10 through a patient's vessels. The floppy tip 28 can be aimed in different directions by rotating the catheter or by actuating a steering mechanism (not shown). The floppy tip 28 is preferably formed from a flexible coil spring which is radiopaque so as to be visible under fluoroscopy. The floppy tip 28 is held in place by thermally forming the imaging portion 26 over the floppy tip 28 or alternatively using any other suitable attachment technique such as adhesives, press fit, connectors, fasteners, etc. In an alternative form, the guidewire 10 is constructed without the floppy tip 28 leaving the distal extremity greater flexibility. In this case, a radiopaque maker band is placed at the distal end of the imaging portion 26.

The imaging core 18 principally comprises a tubular drive shaft 44 having an imaging device 42 attached to a distal end of the drive shaft 44 and the connector 40 attached to a proximal end of the drive shaft 44. The drive shaft 44 may be composed of a single tubular member (not shown); or preferably, it may be several elements attached together as shown in FIGS. 1–3. A telescope portion 48 of the drive shaft 44 is preferably formed of a NITINOL tube having an outer diameter of approximately 0.022".

The telescope portion 48 acts as a telescoping extension of the drive shaft 44 and is of a length approximately the same as the desired length of axial translation of the imaging device 42, preferably around 15 cm. The telescope portion 48 is connected to the connector 40 at its proximal end and extends distally to a distal end which is attached to a proximal end of a drive cable 50. The drive cable 50 is preferably of a counterwound, multifilar coil construction as best shown in FIG. 3 and described in U.S. Pat. No 4,951,677, to Crowley et al., the disclosure of which is incorporated herein by reference. The telescope portion 48 is attached to the drive cable 50 using a coupler 52. One end of the coupler 52 is attached to the telescope portion 48 using an interference fit. The interference fit may be accomplished by cooling the NITINOL telescope portion 48 below its transition temperature such that it becomes soft. The coupler 52 is then slid onto the telescope portion 48 and when warmed above the transition temperature, a secure interference fit results. The other end of the coupler 52 is attached to the drive cable 50, preferably using an adhesive, although any suitable attachment means is contemplated. The coupler 52 also functions as a stop which interferes with a stop collar 42 attached to the inside of the proximal end 22 of the main body 20 which limits the proximal axial translation of the imaging core 18 relative to the guidewire body 16. The stop collar 42 may also be interference fit into the NITINOL main body 20 using the same method just described for attaching the coupler 52 to the telescope portion 48.

The imaging device 42 is attached to the distal end of the drive cable 50. The imaging device 42 may be any type device which creates a high quality imaging signal of the body tissue to be imaged, but is preferably an ultrasound imaging device. The imaging device 42 includes a housing into which an ultrasound transducer 56 is mounted. The design, construction and use of ultrasound imaging devices is generally known in the art and therefore a detailed description is not included herein. The ultrasound transducer 56 is oriented to image in a radially outward direction and when rotated with the drive shaft 44 creates a 360 degree radial scan of the surrounding tissue. Alternatively, the ultrasound transducer 56 may be oriented such that it images in a forward looking or backward looking direction or any angle in between.

To transmit the imaging signal from the imaging device 42 to the connector 40, a coaxial cable 58 is attached to the imaging device 42 which runs down the center of the drive shaft 44 where the other end of the coaxial cable 58 is attached to the connector 40. The connector 40 detachably connects to a drive unit (not shown) and/or imaging signal processing equipment (not shown).

Turning now to FIG. 2, the innovative connector 40 will be described in detail. Overall, the connector 40 is cylindrically shaped and has a maximum diameter not exceeding the diameter of the remainder of the guidewire 10, which is preferably 0.035" in diameter. The distal end of the connector 40 is composed of a conductive ring 60 which is attached to the proximal end of the telescope portion 48 by an interference fit as shown, or by any other suitable attachment method. The conductive ring 60 is filled with conductive epoxy 62 through a fill hole 80 to cover the outer lead 64 of the coaxial cable 58 thereby electrically connecting the conductive ring 60 to the outer lead 64 and completing one pole of the imaging device 42 circuit. The conductive ring 60 may have a second hole 82 to observe the amount of epoxy being inserted to ensure that it does not overfill and electrically connect to a second conductor 66. The second conductor 66 has a stepped tubular section 70 and a ball-shaped end 72. The stepped tubular section 70 is covered with an insulator 74 such as a piece of shrink tubing. The stepped tubular section 70 covered with the insulator 74 inserts into the conductive ring 60 and bonded in place using an adhesive such as cyanoacrylate. The insulator 74 electrically insulates the conductive ring 60 from the second conductor 66. The inner lead 68 and insulation 76 of the coaxial cable 58 extend through the first conductive epoxy 62 and through the stepped tubular section 70. The inner lead 68 further extends into a cavity in the ball-shaped end 72. The cavity in the ball-shaped end 72 is filled with a second conductive epoxy 78 to conductively connect the second conductor 66 to the inner lead 68 completing the other pole of the imaging device 42 circuit.

Hence, connector 40 provides a detachable electrical and mechanical attachment to the drive unit (not shown) which rotates the imaging core 18 and to the signal processing electronics (not shown). The detachability feature allows the guidewire 10 to be quickly and easily disconnected so that catheters may be inserted over the guidewire 10 and, then just as easily, the guidewire 10 can be reconnected.

The imaging core 18 is slidably and rotatably received within the guidewire body 16 such that the imaging core 18 may be axially translated relative to the guidewire. In this way, the imaging device 42 can be axially translated along the imaging portion 26 of the guidewire body 16 thereby enabling imaging along an axial length of a region of tissue without moving the guidewire body 16. Hence, the proper positioning of the guidewire 10 within the patient's body is maintained so that it may effectively serve as a guidewire for the insertion of catheters.

An alternative embodiment of an imaging guidewire 90 is shown in FIGS. 4–5. The imaging guidewire 90 is similar to, and includes many of the features and elements as, the imaging guidewire 10 described above. Throughout the description and figures, like reference numerals refer to like elements and therefore, some elements are not explicitly described for all figures.

The main differences of the imaging guidewire 90 are the use of a single polymer sheath 94 for the guidewire body 92, and a modified imaging core 96. The guidewire body 92 is formed of a single piece polymer sheath 94 having a proximal end 98 and a distal end 100. Preferred polymer sheath materials include polyimide and PEEK. The sheath 94 extends from the connector 40 to the distal end of the guidewire 90. A nonrotating union collar 104 may be inserted between the rotatable connector 40 and the nonrotating sheath 94 to limit wear of the polymer sheath at the intersection between the connector 40 and the sheath 94.

The imaging core 96 comprised a drive cable 102 having the imaging device 42 attached to its distal end and the connector 40 attached to its proximal end. The drive cable 102 is preferably a counterwound, multifilar coil as described above. A stiffening sleeve 106 preferably formed of a flexible tube such as a NITINOL tube, is disposed between the drive cable 102 and the sheath 94. The polymer sheath 94 may not provide sufficient rigidity and pushability to the guidewire and therefore, the stiffening sleeve 106 gives the guidewires these properties. The stiffening sleeve 106 is received into the union collar 104 and extends distally to the imaging device 42. In an alternative form, the stiffening sleeve 106 could extend distally to a predetermined distance short of the imaging device 42, preferably about 15 cm short. The stiffening sleeve 106 preferably does not rotate with the drive cable 102.

The method of using the imaging guidewire 90 is virtually identical to that described above for imaging guidewire 10.

FIGS. 6–7 show an imaging guidewire 10 having an improvement in the transition from the stiffer main body 20 of the guidewire body 16 to the softer, more pliable imaging portion 26 according to the present invention. A relatively large difference in the stiffness of the main body 20 and the imaging portion 26 can create a stress riser at the connection point which tends to cause the more flexible imaging portion 26 to bend sharply and/or kink when the guidewire is routed through small radius paths. To relieve this condition, instead of bonding the imaging portion 26 directly to the main body 20 as described above, a graduated transition 120 comprising a short transition tube 108 is attached to the distal end 24 of the main body 20 and the imaging portion 26 is attached to the other end of the transition tube 108. The transition tube is made of a material, and is configured, such that is has a stiffness between that of the main body 20 and the imaging portion 26.

FIGS. 8–9 show an alternative configuration for the graduated transition 120 between the main body 20 and the imaging portion 26 similar to that described with respect to FIGS. 6–7, except that the distal end of the transition tube 110 is left free. The outer diameter of the main body 20 is reduced from that described above to accommodate a full length jacket 112 comprising a thin layer of plastic, preferably polyethylene, to be formed over the entire length of the main body 20. The preferred reduced thickness of the main body 20 is preferably about 0.032" corresponding to a jacket 110 thickness of about 0.003". The imaging portion 26 and the jacket 112 may be formed from a single varying thickness piece of material. In this configuration, the transition tube 110 is similar in construction and materials to the transition tube 108 described above.

Another variation of a graduated transition 120 between the main body 20 and the imaging portion 26 is shown in FIGS. 10–11. The imaging guidewire 10 of FIGS. 10–11 is identical to that shown in FIGS. 1–3 except that the distal end 24 of the main body 20 is constructed in a spiral form 114 with increasing pitch as it extends distally. Then, the imaging portion 26 extends over the spiral form 114. The spiral form 114 creates a more flexible portion of the main body 20 which performs the graduated transition function similar the that described above.

FIGS. 12–13 depict yet another embodiment of an imaging guidewire 10 having a graduated transition 120. The imaging guidewire 10 of FIGS. 12–13 is identical to that of FIGS. 10–11 except that the spiral form 114 is replaced with a tapered finger section 116.

Still another embodiment of graduated transition 120 on an imaging guidewire 10 is shown in FIGS. 14–15. In this embodiment, a reinforcing braided section 118 is placed over the connection between the imaging portion 26 and the main body 20. The braided section 118 may be made of plastic such as polyethylene, co-extruded polymer materials, or any other suitable material. The braided section 118 performs similarly to the graduated transitions described above.

Except for the varying graduated transition configurations of the guidewire body 16, the imaging guidewires 10 of FIGS. 6–15 are identical to the imaging guidewire described for FIGS. 1–3. In addition, the method of using the imaging guidewires is the same as previously described.

Thus, the reader will see that the present invention provides an improved imaging guidewire. While the above description contains many specifics, these should not be construed as limitations on the scope of the invention, but rather as an examples of particular embodiments thereof. Many other variations are possible.

Accordingly, the scope of the present invention should be determined not by the embodiments illustrated above, but rather, the invention is to cover all modifications, alternatives and legal equivalents falling within the spirit and scope of the appended claims.

What is claimed is:

1. An imaging guidewire comprising:
   a body in the form of an elongate flexible tubular member, said body having a proximal end and a distal end, at least a portion of said body being substantially transparent to imaging energy;
   a flexible elongate imaging core slidably received within said body, said imaging core having a shaft including coaxial cable running down the center thereof and an imaging device mounted on a distal end of said shaft and arranged to position said imaging device in axial relation to said substantially transparent portion of said body, said imaging device adapted to receive imaging energy related to internal body tissue and to transmit imaging signals to an imaging signal processor;
   a connector comprising a first conductor attached to the shaft, the first conductor being electrically connected to an outer lead of the coaxial cable, and a second conductor bonded in place to the first conductor, the second conductor being electrically isolated from the first conductor, the second conductor being electrically connected to an inner lead of the coaxial cable;
   the imaging guidewire having a maximum diameter along its entire length not exceeding that which can effectively be received in a guidewire lumen of an intravascular catheter;
   wherein said imaging core is axially translatable relative to said body to enable axial translation of said imaging device.

2. The imaging guidewire according to claim 1, wherein said imaging device comprises an ultrasound transducer.

3. An imaging guidewire comprising:
   a body in the form of an elongate flexible tubular member, said body having a proximal end and a distal end, at least a portion of said body being substantially transparent to imaging energy;
   a flexible elongate imaging core slidably received within said body, said imaging core having a shaft and an imaging device mounted on a distal end of said shaft and arranged to position said imaging device in axial relation to said substantially transparent portion of said body, said imaging device adapted to receive imaging energy related to internal body tissue and to transmit imaging signals to an imaging signal processor;
   a connector attached to the proximal of said shaft, said connector being configured to provide detachable electrical attachment to said image signal processor while simultaneously providing detachable mechanical attachment to a drive unit arranged to rotate said shaft;
   the imaging guidewire having a maximum diameter along its entire length not exceeding 0.035";
   wherein said imaging core is axially translatable relative to said body to enable axial translation of said imaging device.

4. The imaging guidewire according to claim 3, wherein said imaging device comprises an ultrasound transducer.

5. A method of using an intravascular imaging guidewire to direct a catheter to a desired position within a vessel of a body comprising the steps of:
   positioning an intravascular imaging guidewire within a vessel, the intravascular imaging guidewire comprising a body having a portion thereof substantially transparent to imaging energy and an imaging core having an imaging device attached to the distal end thereof, the imaging core being axially translatable relative to the body to enable axial translation of the imaging device;
   imaging the vessel along an axial length using said imaging core without moving the body of the guidewire; and
   routing a catheter over the intravascular imaging guidewire to the desired position.

6. The method of claim 5, further comprising the step of detaching a proximal end of the intravascular imaging guidewire from a drive unit prior to routing the catheter over the intravascular imaging guidewire.

7. The method of claim 5, wherein the intravascular imaging guidewire is positioned such that a distal end of the intravascular imaging guidewire extends beyond a diseased region of interest with the substantially transparent portion of the body approximately centered at the diseased region of interest.

* * * * *